US009211337B2

(12) United States Patent
Shaver

(10) Patent No.: US 9,211,337 B2
(45) Date of Patent: *Dec. 15, 2015

(54) METHOD, COMPOSITION AND PACKAGE FOR BOWEL CLEANSING

(71) Applicant: Braintree Laboratories, Inc., Braintree, MA (US)

(72) Inventor: William A. Shaver, Lubbock, TX (US)

(73) Assignee: Braintree Laboratories, Inc., Braintree, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/219,468

(22) Filed: Mar. 19, 2014

(65) Prior Publication Data
US 2015/0056307 A1   Feb. 26, 2015

Related U.S. Application Data

(63) Continuation of application No. 13/324,667, filed on Dec. 13, 2011, now Pat. No. 8,753,618.

(60) Provisional application No. 61/462,094, filed on Jan. 28, 2011.

(51) Int. Cl.
| | |
|---|---|
| A61K 35/38 | (2015.01) |
| A61K 33/14 | (2006.01) |
| A61K 47/10 | (2006.01) |
| A61K 9/00 | (2006.01) |
| A61K 33/00 | (2006.01) |
| A61K 45/06 | (2006.01) |

(52) U.S. Cl.
CPC ............... *A61K 47/10* (2013.01); *A61K 9/0095* (2013.01); *A61K 33/00* (2013.01); *A61K 33/14* (2013.01); *A61K 45/06* (2013.01); *Y10S 514/892* (2013.01)

(58) Field of Classification Search
CPC .... Y10S 514/892; A61K 33/14; A61K 45/06; A61K 47/10
USPC ...................................................... 424/78.01
See application file for complete search history.

(56) References Cited

U.S. PATENT DOCUMENTS

| | | | |
|---|---|---|---|
| 5,274,001 A | 12/1993 | Borody | |
| 5,445,805 A | 8/1995 | Zuccarello et al. | |
| 6,946,149 B2 | 9/2005 | Cleveland et al. | |
| 7,169,381 B2 | 1/2007 | Barras et al. | |
| 7,291,324 B2 | 11/2007 | Dennett, Jr. et al. | |
| 8,753,618 B2 | 6/2014 | Shaver | |
| 2005/0003021 A1 | 1/2005 | Sugiyama et al. | |
| 2006/0051428 A1 | 3/2006 | Ayala et al. | |
| 2007/0082061 A1 | 4/2007 | Ayala et al. | |
| 2007/0092543 A1 | 4/2007 | Casana Giner et al. | |
| 2008/0260682 A1 | 10/2008 | Rose et al. | |
| 2009/0258090 A1 | 10/2009 | Cleveland | |

FOREIGN PATENT DOCUMENTS

| | | |
|---|---|---|
| JP | 3-284620 | 12/1991 |
| JP | 2721929 | 12/1991 |
| JP | 2004323456 | 11/2004 |
| WO | WO8700754 | 2/1987 |
| WO | WO0048585 A1 | 8/2000 |
| WO | WO1041751 A1 | 4/2010 |

OTHER PUBLICATIONS

Glenn R. Davis, et al., "Development of a Lavage Solution Associated with Minimal Water and Electrolyte Absorption or Secretion," Gastroenterology, 78:991-995 (1980).
Marc-Andre Bigard, et al., "Fatal Colonic Explosion During Colonoscopic Polypectomy," Gastroenterology, 77:1307-1310 (1979).
A. Barkun, et al., "Commonly used preparations for colonoscopy: Efficacy, tolerability and safety—A Canadian Association of Gastroenterology position paper," Can. J. Gastroenterol, 20(11):699-710 (2006).
Jack DiPalma, et al., "A Randomized Clinical Study Evaluating the Safety and Efficacy of a New, Reduced-Volume, Oral Sulfate Colon-Cleansing Preparation for Colonoscopy," The American Journal of Gastroenterology, 104:2275-2284 (2009).
M.R. Islam, "Cirtate can effectively replace bicarbonate in oral rehydration salts for cholera and infantile diarrhoea," Bulletin of the World Health Organization, 64(1):145-150 (1986).
D. Storey, et al., "Gastrointestinal tolerance of erythritol and xylitol ingested in a liquid," European Journal of Clinical Nutrition, 61:349-354 (2007).
K.K. Makinen, Long-Term Tolerance of Healthy Human Subjects to High Amounts of Xylitol and Fructose: General and Biochemical Findings, Int. Z. Vitam. Ernahrungsforsch. Beih., 15:92-104 (1976).
International Search Report dated Jul. 31, 2012 for PCT/US2011/064670.
Marcia Gruber et al., "Palatability of Colonic Lavage Solution Is Improved by the Addition of Artificially Sweetened Flavored Drink Mixes," Society of Gastroenterology Nurses and Associates, pp. 135-137 (1991).
International Preliminary Report on Patentability dated Jun. 14, 2013 for PCT/US2011/064670.
Soga, Yasushi et al, Electrolytes for purgatives, Database Caplus Chemical Abstracts Service, Columbus, Ohio, US; Database accession No. 1992:113585.

*Primary Examiner* — Gina Justice
(74) *Attorney, Agent, or Firm* — McCarter & English, LLP; Maria Laccotripe Zacharakis; Maneesh Gulati

(57) ABSTRACT

The present invention provides a highly palatable colon cleansing formulation that utilizes a low chloride electrolyte-replenishing base solution. When formulated with polyethylene glycol and a selected sugar alcohol, the formulation offers the advantages of superior palatability without undesirable concomitant side effects or a decrease in cleansing efficacy.

54 Claims, No Drawings

METHOD, COMPOSITION AND PACKAGE FOR BOWEL CLEANSING

RELATED U.S. APPLICATION DATA

This application is a continuation of U.S. patent application Ser. No. 13/324,667, filed on Dec. 13, 2011, which claims the filing date benefit of U.S. Provisional Application Ser. No. 61/462,094, filed Jan. 28, 2011, the contents of each of which are hereby specifically incorporated by reference herein in their entirety.

BACKGROUND OF THE INVENTION

1. Field of the Invention

The present invention relates to an improved method, composition, package, and kit for colon evacuation and cleansing prior to colonoscopy, or in preparation for other medical, radiologic and/or surgical procedures.

2. Introduction

Deaths from colon cancer have been declining since the mid-1980's due to the widespread use of colonoscopy for both earlier detection of existing cancers, and removal of premalignant colon polyps detected by screening colonoscopy. As a result, the American Cancer Society recommends that all persons over 50 years of age undergo a screening colonoscopy every 10 years. An estimated 42 million Americans have not yet undergone this recommended screening colon examination to date. One reason patients avoid scheduling this very important examination is a reluctance to undergo the thorough bowel cleansing that is required before the examination. Anecdotal stories of the salty and disagreeable taste of the commercially available colon cleansing solutions patients are required to drink prior to the examination abound, and the palatability of these products are a major reason patients avoid scheduling this potentially life-saving examination.

In most medical or surgical procedures involving the colon, cleanliness is an important prerequisite for various reasons: i.e., in colonoscopy cleanliness is essential for a complete and accurate examination as retained stool or particulate matter can easily mask or hide polyps or flat cancers; and in colorectal surgery cleanliness is very important to facilitate a sterile operation. An ideal bowel cleanser would be effective, ensuring complete and accurate visualization of the colonic mucosa, safe for all patient groups, including those with diabetes or compromised renal function, acceptable to patients, and reasonably priced. A better tasting solution would be even more preferred.

3. Description of the Related Art

Many different methods have been utilized in the past to cleanse the bowel prior to medical or surgical procedures, including the use of various laxatives, enemas, suppositories and/or prolonged dietary manipulations. Large volumes of 0.9% saline solution or poorly absorbed saccharides such as mannitol or sorbitol were administered in the past, but significant absorption or loss of fluid and electrolytes as a result of ingesting these kinds of preparations sometimes resulted in serious complications in elderly debilitated patients or those with cardiopulmonary problems. The modern era of colon cleansing was heralded by Davis and Fordtran in 1980 with the development of osmotically-balanced large volume solutions where there was no net absorption or secretion of fluid or electrolytes. (Davis G L, *Gastroenterology:* 78:991-995, 1980).

Colon cleansing solutions may be contrasted on the basis of their osmotic balance, or tonicity. Osmolality is a measure of the number of dissolved particles in a fluid and is measured as mOsm/kg. Osmolality can be directly measured using standard laboratory techniques such as freezing point depression or calculated from knowledge of the individual dissociated ions present in the solution. The osmotic activity of human serum or plasma is measured in mOsm/liter and is referred to as osmolarity. Normal human serum osmolarity is around 285-295 mOsm/L. Tonicity refers to the osmotic pressure created by solutions of differing osmolalities on either side of a semi-permeable membrane. Based on tonicity, colon cleansing solutions can be classified as isotonic, hypertonic, or hypotonic. Isotonic solutions have an equal balance of impermeable molecules on either side of a semi-permeable membrane and thus are in balance with the vasculature of the intestine and do not lead to any net absorption or loss of fluid or electrolytes from the body. Hypertonic solutions contain a greater concentration of impermeable solutes than the surrounding fluid, and have the potential to draw fluid into the intestine, a process that can potentially dehydrate a patient and concentrate the serum electrolytes. Hypotonic solutions contain a lower concentration of impermeable solutes than the surrounding fluid and can lead to excess absorption of free water from within the intestine and undesirable dilution of the serum electrolytes. Each general category of colon cleansing solutions has advantages and disadvantages, but the sheer number of variations described in the prior art attest to the fact that an ideal formulation has yet to be created that is effective, safe, and well tolerated by a majority of patients.

Isotonic or balanced colon lavage solutions as originally described by Davis and Fordtran contain a combination of electrolytes and a water soluble, poorly absorbed solute, generally polyethylene glycol ("PEG") that is in osmotic balance with the normal serum concentrations of electrolytes in the vasculature of the intestinal tract. PEG is a complex, non-absorbed, inert polymer of ethylene oxide that works by attracting and holding the water ingested with the lavage solution within the lumen of the intestine through osmotic effects. The quantity of PEG contained in these solutions is typically adjusted with the electrolytes so that the osmolality of the final solution approximates that of normal human serum, or around 285-295 mOsm/L. Standard PEG-containing formulations include the formulation GoLYTELY®, based on the formula originally proposed by Davis and Fordtran and commercialized by Braintree Laboratories of Braintree, Mass., and a more recent Braintree formulation NuLYTELY® based on the patent (WO/1987/000754) by Fordtran which omits the sodium sulfate in the formulation and increases the amount of PEG in the final solution to maintain isotonicity. Other known formulations with PEG include a formulation provided by Alaven Pharmaceutical, LLC (Marietta, Ga.) under the trademark TriLyte®, and a formulation produced by Schwarz Pharma AG (Monheim, Germany) under the name CoLyte™.

Colon cleansing is achieved by the consumption of large volumes of these solutions, but as the solutions are isotonic, they do not cause any net water gain or loss within the lumen of the intestine. As a result, patients do not experience dehydration or major fluid or electrolyte shifts when these solutions are consumed, and they have been proven to be safe even when used with patients with cardiopulmonary, kidney, or fluid volume problems. However, patients find consumption of these isotonic solutions difficult to complete. The salty and bitter taste that occurs as a result of the electrolytes that are part of these formulations contribute to the nausea, vomiting, and bloating that patients often experience when consuming this type of solution, and even when these side effects do not occur, patients often complain that consumption of such solutions is extremely unpleasant.

In one attempt to address these difficulties, Braintree Laboratory introduced HalfLYTELY®, based on U.S. Pat. No. 7,291,324 by Dennett et al., in which bisacodyl delayed release tablets (Dulcolax®) are administered several hours prior to the patient's consumption of the lavage solution. Dennett et al. claims that the volume of solution that has to be consumed can be decreased from four to two liters and still produce adequate cleansing.

A different isotonic formulation described in U.S. Pat. No. 5,274,001 by Borody incorporates ascorbic acid/or a salt of ascorbic acid as osmotically-active solutes, in addition to PEG and sodium sulfate. Brody et al. report that ascorbic acid in this formulation acts as an additional osmotic agent that allows one to decrease the amount of fluid that has to be consumed to three liters. This formulation has been sold in Australia under the trade name GlycoPrep C™ (Pharmatel LLC, Sydney, Australia) for several years.

Hypertonic colon cleansing formulations contain high concentrations of osmotically-active solutes that, when consumed, draw and retain large amounts of water from the patient's circulation into the lumen of the intestinal tract, which then distends the colon, stimulates peristalsis, and evacuates the contents of the colon. Whereas isotonic formulations incorporate the volume of required fluid as part of their formulae requiring two to four liters to do so, hypertonic solutions draw a large part of the required fluid from the patient. As a result, such formulations have the potential to cause sudden fluid and electrolyte shifts, dehydration, and concentration of the electrolytes in the serum, which can result in permanent kidney damage or even death in certain patients if preparations are consumed without ingestion of sufficient additional water.

An older hypertonic method of colon cleansing involved the ingestion of solutions that contained hypertonic concentrations of poorly absorbed, but potentially fermentable 6-carbon sugar alcohols such as mannitol or sorbitol. Reports of colonic explosion and death as a result of hydrogen and methane gases formed from the fermentation of these substances by the bacterial flora ignited by the electrocautery used at the time of polypectomy (Bigard M A, et al., *Gastroenterology* 77:1307-1310, 1979), led to a general consensus that simple or complex sugars should not be utilized in colon lavage solutions.

The most widely utilized hypertonic colon cleansing agents contain a concentrated aqueous solution of phosphate salts in liquid or tablet form (NaP), and therefore minimize the problems/complaints associated with large-volume PEG solutions. The C.B. Fleet Company (Lynchburg, Va.) manufactured and sold Fleet Phospho-Soda®, which is comprised of 480 gms/L of monobasic sodium phosphate and 180 gms/L of dibasic sodium phosphate. Randomized, controlled trials of this formulation were reported to demonstrate equivalent efficacy and superior tolerability solutions when compared with the larger volume PEG-containing solutions. (Barkun A., *Can. J Gastroenterol.* 20(11):699-710, 2006). However, this formulation had an extremely salty and unpleasant taste. In addition, the high concentration of phosphate salts in this type of formulation produced a large influx of fluid and electrolytes into the lumen of the intestine from the patient's circulation, resulting in problems with dehydration, metabolic derangement, kidney damage, and even some reported deaths which prompted the FDA to issue a safety warning on Fleet Phospho-soda. The C.B. Fleet Company has subsequently recalled this product from the market. Salix Pharmaceuticals, LLC (Morrisville, N.C.) continues to sell a tablet form of a sodium phosphate commercialized as Osmoprep® that carries a black box warning. Visicol® is another tablet preparation of NaP sold by InKine Pharmaceutical Company (now merged with Salix Pharmaceuticals, LLC).

U.S. Pat. No. 6,946,149 by Cleveland describes a smaller volume, hypertonic solution that avoids the adverse effects of the high sodium phosphate in prior art formulations by incorporating a mixture of sulfate salts (sodium, potassium, and magnesium sulfates) in place of phosphate salts in the formulation. In a later patent application, US 2009/0258090, Cleveland also incorporates 0.01%-0.1% by weight of an artificial sweetener from a group of chlorinated sucrose isomers that includes saccharin and/or Sucralose to this mixture of sulfate salts and PEG, and thereby lowers the perceived saltiness of the solution to the equivalent of about 0.2% to 2.6% sodium chloride in water. Braintree Laboratories has recently commercialized this formulation as Suprep®, and FDA approval was only recently granted for this product in August of 2010. Patients are required to consume 3 total liters of fluid when utilizing the Suprep® method of colon cleansing (1 liter of Suprep® in split-dose fashion with each 500 ml dose of Suprep® followed with 1 liter of water). Cleansing and completion results were the same when compared to Movieprep® or isotonic PEG-containing lavage solutions, but vomiting was slightly more common in the Suprep® group (DiPalma J A, Rodriguez R, McGown J, and Cleveland M., *American Journal Gastroenterology*, 104:2275-2284, 2010).

U.S. Pat. No. 7,169,381 by Barras describes a 2 liter hypertonic composition that contains ascorbic acid or salts of ascorbic acid, an alkali metal sulfate, and certain electrolytes in addition to PEG. Barras reports that this formulation is equal in efficacy to previous 3 or 4 liter compositions without requiring a preceding dose of bisacodyl (Dulcolax®). This composition has been commercialized and sold by Salix Pharmaceutical, LLC as Movieprep®. The sodium sulfate and ascorbic acid components in Movieprep®, however, still give the solution a salty lemon-lime taste that many patients find disagreeable, and nausea and vomiting of this preparation has also been noted. (See DiPalma reference above.)

A different type of colon cleansing solution has been described in Japanese Patent 2721929. This formulation incorporates the minimally-fermentable sugar alcohols xylitol and/or erythritol in a concentration of from 5.0-35.0 grams per liter as well as a corresponding amount of sodium and potassium electrolytes to maintain isotonicity. These sugar alcohols were specifically utilized in the composition to avoid the use of PEG in colon cleansing solutions. The lower concentrations of xylitol and/or erythritol claimed would require a concomitant increase in sodium sulfate and/or additional electrolytes to maintain isotonicity, at the cost of increasing the salty taste and decreasing the palatability of the final solution.

As a result of these multiple ongoing problems with the existing art, a growing number of physicians are utilizing a non-FDA approved hypotonic mixture of a proprietary PEG 3350 product Miralax® (Braintree Laboratory), mixed with a 2 liter volume of Gatorade® or other sports drink/rehydration solution as an electrolyte source (PEG-ELS). This colon cleansing solution is, on belief, better tasting (as it contains sugar and little salt), is inexpensive, and can be prepared by the patient from all over-the-counter products. Most sport drink/electrolyte solutions contain up to 6% carbohydrates, however, including high-fructose corn syrup which is believed to prompt several health problems, and particularly so in diabetic patients, as well as carry the risks of fermentation by the bacterial flora in the colon into potentially explosive hydrogen and methane gas. In addition, the relatively low concentration of electrolytes and dilute nature of these hypotonic formulas can lead to excess absorption of free water and result in significant fluid overload, hemodilution, and serious electrolyte imbalance, including low serum sodium levels (hyponatremia) which can cause swelling of the brain, confusion, seizures, and rarely, death. Despite these concerns, the non-FDA approved use of PEG-ELS continues to grow.

Therefore, there remains a need in the art for a colonic cleansing formulation that has the following advantages:
1) improves the quality of bowel cleansing prior to colonoscopy, surgery, or radiologic examinations;
2) provides improved taste to encourage patients to consume the entire preparation as prescribed;
3) is easy and convenient for patients to prepare;
4) avoids the risk of creating potentially explosive gases from bacterial fermentation of the solution;
5) does not impact insulin levels or raise blood sugar levels in diabetic patients; and
6) is safe.

SUMMARY OF INVENTION

The present invention overcomes the disadvantages of prior solutions by providing a colon cleansing formulation that is not only better tasting, but is also more balanced in electrolyte composition, safer for patients with diabetes or other serious medical conditions, and is convenient to prepare. By incorporating potassium bicarbonate instead of potassium chloride, and combining an organic acid such as citric acid with sodium bicarbonate to produce tri-sodium citrate as an alternate electrolyte replenisher, the present invention produces a more palatable electrolyte solution with an advantageously lowered chloride concentration, that, when combined with a suitable concentration of a suitable sugar alcohol, such as xylitol (or alternatively or additionally erythritol, ribitol or arabitol), and polyethylene glycol provides a colon cleansing solution with improved taste and flavor, that, in certain embodiments, has a taste intensity that approaches that of natural water. This highly palatable effervescent isotonic solution can be consumed without additional flavoring, or a higher concentration of the sugar alcohol can be used to create a mildly hypertonic formulation with a pleasant, almost cola-like, taste that functions even more effectively as a purgative with both the PEG and sugar alcohol acting as dual osmotic agents.

The invention includes an ingredient for use in formulating an electrolyte-replenishing solution for an orally administered colon cleanser with greatly improved palatability. By controlling the chloride content of the solution while providing electrolytes sufficient to maintain an appropriate electrolyte balance, the invention offers the advantageous property of encouraging patient compliance in consuming a sufficient amount of the cleanser to result in adequate bowel cleansing for colonoscopy or other medical procedure requiring bowel cleansing without suffering from the disadvantages associated with formulations that do not adequately maintain electrolyte balance in the patients to whom they are administered. Accordingly, the electrolyte-replenishing solution is defined as a solution that contains a sufficient amount of selected serum electrolytes, such as, e.g., sodium, potassium and chloride ions, to prevent an unacceptable change in fluid balance or serum electrolytes in the patient to whom the solution is administered.

Those of skill in the art will also recognize that in addition to the electrolyte-replenishing solution, the oral colon cleanser will typically also include polyethylene glycol as a suitable agent to provide the desired tonicity of the formulation in the intestinal tract. In addition, as mentioned above, a sugar alcohol may be combined with the polyethylene glycol to enhance the purgative effects of the solution. In an alternative embodiment, the sugar alcohol is present in lower amounts which, while not appreciably affecting the purgative effects of the solution, nevertheless contribute an additional advantage of offsetting the undesirable salty taste reported with other formulations used in the field.

In one example, therefore, the invention comprises an ingredient for substantially improving the palatability of an oral colon cleanser and for providing the patient with a needed electrolyte replenishing solution, said ingredient comprising a low-chloride electrolyte component that, when reconstituted in a pharmaceutically acceptable aqueous diluent for oral administration, produces an electrolyte-replenishing base solution which contains no more than about 17 mEq of chloride ions per liter of solution. Typically, the chloride concentration is provided by an appropriately limited amount of a pharmaceutically acceptable chloride salt. In addition, the solution may include one or more non-chloride containing salts selected from a group consisting of potassium bicarbonate, sodium bicarbonate, and mixtures thereof, and an amount of citric acid effective to produce tri-sodium citrate when said salts and said citric acid are dissolved in an aqueous solution. In a more preferred embodiment, the citric acid will be anhydrous citric acid. In an even more preferred embodiment, the mixture will have a perceived saltiness equivalent of between about 0.1% and 0.3% when said mixture is dissolved in one liter of solution, wherein the perceived saltiness equivalent is defined as the saltiness equivalent to a percentage of sodium chloride in water. A perceived saltiness equivalent of 0.3% is therefore equal to the saltiness of a 0.3% sodium chloride solution in water. The composition will typically also contain a mixture of PEG having a molecular weight between about 2000 and 8000 Daltons and a sugar alcohol selected from the group consisting of xylitol, erythritol, ribitol, arabitol, and mixtures thereof. In a more preferred embodiment, the combination of PEG and sugar alcohol will comprise at least 90% by weight of the dry ingredients of the formulation.

In a further preferred embodiment, the invention is provided in dry component form. This embodiment generally includes a source of electrolytes for the solution, as described herein, a bicarbonate reactant, such as citric acid, PEG as a high molecular weight agent to maintain a desired tonicity, and a sugar alcohol, which can advantageously serve to decrease the perceived saltiness of the solution and, in an additional embodiment, enhance the efficacy of the PEG in serving as a colonic purgative. In one particularly preferred embodiment, the dry component will comprise between about 0.15 to 1.5 grams of potassium bicarbonate, 1.0 to 3.5 grams of sodium bicarbonate, 1.0 to 4.0 grams of citric acid, 0.1 to 1.0 grams of sodium chloride, 50 to 140 grams of polyethylene glycol, and 1 to 50 grams of a sugar alcohol. Although xylitol is used in the examples, in other embodiments, the sugar alcohol may be selected from the group consisting of xylitol, erythritol, ribitol, arabitol and mixtures thereof. These amounts are provided per liter of solution to be formulated, and the skilled artisan will readily recognize that the amounts may be adjusted proportionally in accordance with the particular volume of solution to be made and still fall within the ranges encompassed by the claims. In a further preferred embodiment, the composition will comprise between about 1 and about 4 grams per liter of sugar alcohol. In an embodiment in which the sugar alcohol acts to enhance the efficacy of PEG, the concentration or the amount of sugar alcohol can range from about 4 to about 50 grams per liter. Generally, it is preferred that the polyethylene glycol have an average molecular weight of about 2000 to 8000 Daltons, more preferably, about 3000 to 4000 Daltons, and most preferably, about 3350 Daltons. In any event, it also is preferred that when the dry composition is formulated in one liter of an aqueous solution, the solution will have an osmolality of between about 275 and 500 mOsm per kilogram. Moreover, the ratio of polyethylene glycol to sugar alcohol may be adjusted to achieve an ideal balance. For example, in one preferred embodiment, the ratio of polyethylene glycol to sugar alcohol per unit volume of solution will be between about 2:1 to about 60:1, and more preferably between about 1.20:1 and 3.75:1 or, alternatively, between about 25:1 and 75:1.

The invention also includes a solution form. Therefore, there is also provided the ingredient for substantially improving the palatability of an oral colon cleanser and for providing the patient with a needed electrolyte-replenishing solution, said ingredient comprising an aqueous low-chloride electrolyte-replenishing solution of a pharmaceutically acceptable aqueous oral formulation for colon cleansing containing no more than about 17 mEq of chloride ions per liter of solution. Preferably, the solution will have a perceived saltiness equivalent, defined as before, of about 0.1% to 0.3%. The aqueous electrolyte-replenishing solution will typically further include one or more non-chloride containing bicarbonate salts selected from a group consisting of potassium bicarbonate, sodium bicarbonate, and mixtures thereof, as well as citric acid. In such a solution, tri-sodium citrate is created through a reaction of the citric acid and the bicarbonate salt in said solution. Even more preferably, such a solution will include between about 1.5-20 mEq of $Cl^-$ ions (most preferably less than about 20 mEq), between about 10-60 mEq of $Na^+$ ions, between about 1.5-15 mEq of $K^+$ ions, between about 10-60 mEq of $HCO3^-$ ions, and a sufficient amount of citric acid to result in formation of tri-sodium citrate per one liter unit volume. An even more preferred composition will contain between about 35-55 mEq of $Na^+$ ions, between about 15-20 mEq of $Cl^-$ ions, between about 5-10 mEq of $K^+$ ions, and between about 10-20 mEq of $HCO3^-$ ions, per liter of solution. Although a number of pharmaceutically acceptable ion donors may be used to achieve the desired ionic concentration, sodium and/or potassium salts of bicarbonate and/or chloride are preferred. Again, the preferred osmolality of the solution is between about 275-500 mOsm/kg. Typically, the solution will also be formulated to contain between about 50-140 grams per liter of a polyethylene glycol having a molecular weight between about 2000 and 8000 Daltons and between about 1-50 grams per liter of a sugar alcohol selected from the group consisting of erythritol, xylitol, ribitol, arabitol and mixtures thereof. An especially preferred solution will contain about 1 gram per liter NaCl, between about 0.5 and 0.75 grams per liter KHCO3, between about 1.5 and 2.5 grams per liter NaHCO3, and between about 1.5 and 2.5 grams per liter citric acid. Such a solution will typically also include polyethylene glycol having a molecular weight of between about 3000 and 4000 Daltons and xylitol as the sugar alcohol. In one alternative of this formulation, such a solution will contain between about 110-120 grams per liter of polyethylene glycol having a molecular weight between about 3000 and 4000 Daltons and between about 1 and 3 grams per liter of xylitol. Alternatively, the solution may contain between about 60-75 grams per liter of polyethylene glycol having a molecular weight between about 3000 and 4000 Daltons and between about 20-40 grams per liter of xylitol.

Each of the formulations of the invention may be formulated in a manner such that it is substantially free of sulfate ions, substantially free of phosphate ions, substantially free of magnesium ions, or substantially free of all such ions. Ideally, such compositions will not depend on the presence of such ions to achieve or enhance the purgative effect of the formulation and are thus understood to be substantially free of such ions for the purposes described herein, although minor amounts of salts containing such ions may be present as inert ingredients, e.g., as binders, in certain formulations.

The invention also comprises a method for preparing an aqueous solution for colonic cleansing comprising dissolving per liter unit of an aqueous solvent between about 0.15 to 1.5 grams of potassium bicarbonate, between about 1.0 to 4 grams of citric acid, between about 1.0 to 3.5 grams of sodium bicarbonate, between about 0.1 to 1.0 grams of sodium chloride, between about 50.0 to 140.0 grams of polyethylene glycol having molecular weight of between about 2000 and 8000 and between about 1.0 through 50.0 grams of xylitol, erythritol, ribitol, arabitol or mixtures thereof. Those of skill in the art will recognize that an aqueous solvent is water-based, although it may also contain additional ingredients such as flavorings, etc. Accordingly, any of a number of aqueous solutions suitable for use in reconstituting a solution for oral administration known in the art may be used in addition to pure water.

In an additional embodiment, there is provided a convenient method for preparing the aqueous solution for colonic cleansing comprising mixing a dry composition containing between about 1.0 to 4.0 grams of citric acid, between about 0.15 to 1.5 grams of potassium bicarbonate, between about 1.0 to 3.5 grams of sodium bicarbonate, between about 0.1 to 1.0 grams of sodium chloride, between about 50 to 140.0 grams of polyethylene glycol having a molecular weight of between about 2000 to 8000, and from about 1.0 to 50.0 grams of xylitol, erythritol, ribitol, arabitol or mixtures thereof per liter unit volume of aqueous diluent, and allowing said components to substantially dissolve in said diluent.

Even more preferably, one or more of the citric acid, potassium bicarbonate and/or sodium bicarbonate components will be added to the aqueous diluent within a sufficiently short period of time prior to ingestion of the solution such that the ingested solution retains a degree of effervescence immediately prior to ingestion.

A preferred methodology for cleansing of a patient's bowels such as in preparation for colonoscopy or a medical, surgical or radiological procedure, comprises administering to a patient a solution of the invention. In an additional preferred embodiment, an effective amount of a stimulant laxative, such as bisacodyl or other suitable laxative, can be administered about a day before the planned procedure to produce a bowel movement. Then, about 4 to 6 hours after the first administration, and preferably after the bowel movement, a first liter of the composition of the invention will be administered. On the morning following administration of said first liter, a second liter of the composition of the present invention will be administered. In an even more preferred embodiment, the solution is consumed at a rate of about 250 milliliters every 15 minutes until a liter volume is consumed. Of course, those of skill in the art will recognize that the administration need not be, and generally will not be, performed by a second person but may be performed by the recipient of the formulation, i.e., self-administered. Preferably, completion of the consumption of a second liter of the solution should generally be completed by at least about 3 hours prior to a scheduled medical procedure. In an alternative embodiment, the stimulant laxative is administered on the evening before the scheduled procedure, and on the following morning and at least about 6 hours before the procedure is scheduled to occur, 2 liters of the composition is administered at a rate of 250 milliliters every 15 minutes until a sufficient amount of the entire two liter volume to substantially cleanse the colon of said patient, has been consumed by the patient.

The invention also includes a kit for administration of the present invention. For example, in an illustrative embodiment the kit can contains a first container sufficient to hold a volume of at least one liter of the solution, a first mixture of polyethylene glycol, sodium chloride, and a selected sugar alcohol and a second mixture of potassium bicarbonate, sodium bicarbonate, and citric acid. In an even more preferred embodiment, the citric acid is present in an anhydrous form. Alternatively, in one embodiment, the polyethylene glycol, sodium chloride, and sugar alcohol are present in the form of sachets or packets and a mixture of potassium bicarbonate, sodium bicarbonate, and anhydrous citric acid is provided in tablet form. In an alternative embodiment, the kit may contain one or more sachets wherein the sodium and potassium bicarbonate portion of the composition are not present in the same sachet with the anhydrous citric acid. In another preferred embodiment, all of the components of the invention are sealed in a single, air-tight, moisture free sachet. These various embodiments serve to maximize the stability of the anhydrous citrus acid in the presence of the bicarbonates.

DETAILED DESCRIPTION OF PREFERRED EMBODIMENTS

Preparation for procedures used for routine screening examinations such as colonoscopy must not only be safe, but also tolerable to ensure participation by an otherwise healthy, asymptomatic population. Unfortunately, despite the many choices in colon cleansing methods and formulations, around 10-15% of attempted colonoscopies are still compromised due to inadequate cleansing (Bels J., *J Aliment. Pharm. Ther.*, 25:373-384, 2007), and there continues to be significant problems with patient tolerance, ongoing safety concerns and side-effects, as well as the relatively high costs of the compositions in the prior art. The unpleasant and salty taste of the existing art colon cleansing solutions, often poorly masked with artificial sweeteners or flavorings, continue to be a significant impediment for patients contemplating undergoing a colonoscopy. Improving the taste of these solutions might lead to greater patient acceptance and an increased success in screening the general population for colon cancer.

In an attempt to address these problems with the existing art, the inventor has discovered that a novel combination of the present invention creates a colon cleansing solution that is safer than the commonly used Gatorade®/Miralax® preparation, better tolerated than other prescription PEG-containing solutions, and much better tasting than either previous type of solution. The particular unique mixture of components described in this invention combine to create a significantly less salty taste as well as a lower taste intensity when compared to the existing art colon cleansing solutions.

The invention described herein, therefore, represents not only a more palatable colon lavage solution, but even more remarkably, can be formulated to provide a composition with a perceived saltiness equivalent from about 0.1% to 0.3% sodium chloride in water solution. A higher concentration of sugar alcohol in an alternate embodiment of the invention can serve as an additional osmotic agent to produce an even more effective purge with very few side effects such as the nausea and vomiting noted in other prior art solutions, and improves the taste to an even greater degree. The present invention as described represents the first time that a sugar alcohol has been combined in a hypertonic formulation with PEG as dual osmotic agents.

The invention also includes an easy method for mixing and administering the composition as well as a kit suitable for use in preparation for colonoscopy or a medical, surgical or radiological procedure.

In a preferred embodiment, the formulation includes a combination of potassium and/or sodium bicarbonate, sodium chloride, PEG, citric acid, and a suitable sugar alcohol selected from the group consisting of xylitol, erythritol, ribitol, arabitol and mixtures thereof, and an aqueous solvent. Preferably these ingredients will be formulated to produce a solution that ranges from slightly hypotonic to hypertonic while still maintaining an appropriate electrolyte balance in the serum of the patient to which it is administered.

A composition of the invention preferably comprises potassium and/or sodium bicarbonate salts, and more preferably, a combination of both. When potassium bicarbonate is used, it can be present in a quantity of between about 0.15-1.50 grams per liter or more, or more preferably about 0.50-1.0 grams per liter, most preferably about 0.688 grams per liter. When sodium bicarbonate is used, it can be present in a quantity of about 1.0-3.5 grams per liter, or more preferably in a quantity about 2.0-2.5 grams per liter, and even more preferably about 2.1 grams per liter.

In a further preferred embodiment, the composition of the invention preferably comprises citric acid, preferably in anhydrous form. When used, anhydrous citric acid component is present in a quantity of about 1.0-4.0 grams per liter and more preferably about 1.5-3.0 grams per liter. Anhydrous citric acid is most preferably present in a quantity of about 2.0 grams per liter. When added to the formulation with sodium in an aqueous medium, the reaction between the anhydrous citric acid and sodium bicarbonate in the solution produces tri-sodium citrate as well as effervescent $CO_2$ gas. This effervescence has been advantageously found to improve the palatability of the composition, a property that encourages patients to consume the entire volume of solution to achieve the highest quality colon cleansing. In addition, the tri-sodium citrate created when the dry powder composition of the invention described herein is mixed in water creates an additional bicarbonate substitute to aid in the maintenance of proper electrolyte balance and rehydration, yet does not add excessive additional sodium taste to the composition. This is a significant improvement, as the other existing cleansing solutions that contain higher concentrations of sodium in the form of sodium chloride, sodium sulfate, and sodium bicarbonate, have significant problems with palatability and compliance. Tri-sodium citrate has been utilized as a bicarbonate substitute in oral rehydration solutions (ORS) recommended by the World Health Organization and has been used in the treatment of patients with severe diarrhea and acidosis (Islam, M R., *Bulletin of the World Health Organization*, 64(1):145-150, 1986). A fall in serum bicarbonate concentration has been noted following the use of certain of the prior art cleansing solutions such as 0.9% saline or mannitol and, to a lesser degree, Movieprep®. This loss of bicarbonate in the rectal effluent can potentially have serious clinical consequences including a reduced ability to maintain proper blood pH (acidosis), and result in nausea, vomiting, weakness, disorientation and dehydration.

A composition of the invention may also comprise sodium chloride as a source of sodium and chloride ions. When used in this manner, sodium chloride is preferably present in a quantity of about 0.10-1.0 gram per liter, and most preferably in a quantity of about 1.0 gram per liter.

this new formulation to other representative chloride-containing PEG lavage solutions is shown in Table I.

TABLE I

Comparison of Present Invention and Representative Chloride-containing Prior Art PEG Solutions

| Formulation | PEG | NaCl | KCl | KHCO3 | NaHCO3 | Na2SO4 | Citrate | ascorbate | Flavoring/ Carbohydrate |
|---|---|---|---|---|---|---|---|---|---|
| Invention | 120 | 1.00 | 0 | 0.688 | 2.10 | 0.0 | 2.0 | 0.0 | 2 gm xylitol |
| GoLytely | 64 | 1.46 | 0.745 | 0.0 | 1.68 | 5.685 | 0 | 0.0 | None |
| NuLytely | 120 | 5.60 | 0.74 | 0.0 | 1.43 | 0.0 | 0 | 0.0 | flavor pak |
| Movieprep | 100 | 2.69 | 1.015 | 0.0 | 0.0 | 7.5 | 0 | 6.1 | aspartame |
| PEG/ELS | 120 | 0.44 | 0.12 | 0.0 | 0.0 | 0.0 | 0 | 0.0 | High fructose corn syrup |

A composition of the invention also comprises a high molecular weight polymer, such as a commercially available polyethylene glycol (PEG). When PEG is used as the high molecular weight polymer, it will most preferably have an average molecular weight of 3350 Daltons. (PEG 3350). While PEG 3350 is a preferred embodiment and used in the examples, PEGs with molecular weights in the range of from about 2000 to about 8000 Daltons, especially between about 3000 and 4000 Daltons, can also be used. PEG is preferably present in a quantity of between about 50.0-140.0 grams, and more preferably about 68.0-120.0 grams per liter of fluid.

A composition of the invention also preferably comprises a sugar alcohol. The sugar alcohol is preferably present in a quantity of between about 1.0-50.0 grams per liter, and more preferably about 2.0-30.0 grams per liter. Xylitol and erythritol are natural occurring sugar substitutes derived from plants that do not raise blood sugar or insulin levels, and are considered safe for diabetics and are preferred. Doses of xylitol as high as 50 grams per day for over two years were reported by Makinen to have no toxic effects in humans. (Makinen K K—. Long term tolerance of healthy human subjects to high amounts of xylitol and fructose. *Int. Z. Vitam. Ernahrungsforsch. Beih.* 15:9-14, 1976). In another study, consumption of erythritol in doses as high as 50 mg was not reported to produce any significant GI symptoms, but doses of xylitol over 35 grams were reported to result in significantly more watery feces than those of erythritol. (Storey D, et al., "Gastrointestinal tolerance of erythritol and xylitol ingested in a liquid," *European Journal of Clinical Nutrition*, 2006: 1-6). Suitable sugar alcohols should not be appreciably fermented by the bacteria in the intestine so as to pose the risk of creating explosive gases noted in certain previous formulations. Ribitol and/or arabitol may also provide acceptable properties for use in the formulation By using a minimally fermentable four or five-carbon sugar alcohol instead of a fermentable sugar, 5-carbon sugar (such as xylose), or a 6-carbon sugar alcohol (such as mannitol or sorbitol), as well as an effective amount of PEG as a second active osmotic agent, the invention described herein makes use of the beneficial effects that occur when two or more osmotic agents are utilized in combination in a colon cleansing formulation. Accordingly, the present invention provides significant improvements resulting from the use of a selected sugar alcohol (instead of a simple or complex sugar) in combination with PEG as compared to colon cleansing formulations presently utilized prior to colonoscopy, or in preparation for a medical, radiologic and/or surgical procedure. A comparison of a particularly preferred embodiment of In the particularly preferred embodiment of the invention set forth above, a dry composition of about 0.688 grams of potassium bicarbonate, about 2.1 grams of sodium bicarbonate, about 2.0 grams of citric acid, about 1.0 gram of sodium chloride, about 120 grams of PEG 3350, and about 2.0 grams of xylitol are admixed in a liter of water or other aqueous medium. Those skilled in the art may recognize that a formulation of the preferred embodiment may be prepared by combining two Alka-Seltzer Gold tablets, a single 1 gram sodium chloride tablet, one 2 gram packet of xylitol, and 120 grams of the proprietary PEG Miralax® reconstituted in one liter of water.

Although Alka Seltzer Gold® (Bayer Aktiengesellschaft, Leverkusen, Germany) was developed and sold as an over-the-counter treatment for heartburn, acid indigestion, or upset stomach for many years, it has been discovered that the components present in this formulation can also be utilized in the proper ratios for a more balanced and physiologic electrolyte replenishment in a colon cleansing solution as described in the present invention. Each tablet of Alka Seltzer Gold contains 1.0 gram of anhydrous citric acid, 0.344 grams of potassium bicarbonate, and 1.05 grams of sodium bicarbonate, and the usual recommended dose is two (2) tablets dissolved in 4 ounces of water as needed for heartburn or indigestion. The bicarbonate present in Alka Seltzer Gold reacts to neutralize hydrochloric acid present in the stomach to form sodium chloride, water and carbon dioxide (CO2) gas which, as understood, encourages eructation and relief of gastric pressure as well as mildly reducing gastric acid. The reaction of the citric acid and bicarbonate in the tablet, when dissolved in a glass of water, is described in the following equation:

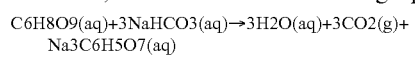

$$C_6H_8O_9(aq) + 3NaHCO_3(aq) \rightarrow 3H_2O(aq) + 3CO_2(g) + Na_3C_6H_5O_7(aq)$$

Citric acid sodium bicarbonate water carbon dioxide trisodium citrate

The effervescence produced by the creation of the CO2 gas has been found to improve the taste and palatability of the product. It is important to note that the only Alka Seltzer product utilized in this particular preferred embodiment is Alka Seltzer Gold, as all other forms of Alka Seltzer contain aspirin in an amount which can be damaging to the gastrointestinal tract mucosa.

A composition of the invention as described above can be prepared in a dry powder form for reconstituting with water or other aqueous medium. The unit dosage of dry powder can be provided in an sealed individual packet or packets or one or more tablets to be mixed in 1 liter of water or other aqueous medium in a pitcher or container of the patient's choice.

In addition to the foregoing ingredients, the formulation of the invention may optionally comprise other ingredients such as coloring or flavoring agents. Suitable flavoring ingredients are natural or artificial compounds, or some combination of these, used to impart a pleasant flavor and/or odor to a preparation. Examples include kola nut extract, cherry flavor extract, caramel flavor extract, anise oil, cinnamon oil, vanilla, vanillin, cocoa, chocolate, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil; citrus oils such as lemon, orange, lime and grapefruit oils, and fruit essences, including apple, pear, peach, berry, wildberry, date, blueberry, kiwi, strawberry, raspberry, cherry, plum, pineapple, and apricot as well as commercially available flavor packs. Suitable coloring agents are compounds used to impart color to solid or liquid preparations. Such compounds include, for example FD&C Red No. 3, FD&C Red No. 20, FD&C Yellow No. 6, FD&C Blue No. 2, D&C Green No. 5, FD&C Orange No. 5, D&C Red No. 8, caramel, and ferric oxide. Coloring agents can also include pigments, dyes, tints, titanium dioxide, natural coloring agents such as grape skin extract, beet red powder, beta carotene, annatto, carmine, turmeric, and paprika.

The present invention may be supplied as a kit, containing two unit doses of the composition in either dry powder, granular, or tablet form along with a suitable container or containers for preparation and administration. The unit dose of the composition may be provided in separate sachets in two or more component form, or contained in a single air-tight and moisture free sachet to maintain the stability of the formulation. The combination of the citric acid and bicarbonates in the formulation in the presence of moisture produces the effervescence. It is preferable to package the composition therefore in an air-tight and moisture-free package or container, or to separate these components in separate sachets until the time of reconstituting the final solution. In one example, the potassium bicarbonate, sodium bicarbonate and citric acid are contained in tablet form in a sealed moisture-proof package and the sodium chloride, PEG, and sugar alcohol contained in a separate sachet. In a second example, the citric acid and bicarbonate components of the formulation are packaged in separate sachets with the remaining components divided between these two sachets. In a third example, all of the solid components of the formulation are packaged in a single airtight and moisture free sachet formulated from any of a variety of air tight containers. The sachet can be vacuum packed to exclude air. A formulation packed in this manner and assayed for electrolyte stability after 30 days showed no change in electrolyte balance.

The compositions included in the kit may be supplied in containers of any sort such that the life of the different components are preserved, and are not absorbed or altered by the materials of the container. For example, suitable containers include bottles that may be fabricated from glass, organic polymers, such as polycarbonate, polystyrene, etc., or any other material typically employed to hold reagents or food; envelopes, that may consist of foil-lined interiors, such as aluminum or an alloy. The containers may have two compartments that are separated by a readily removable membrane that upon removal permits the components to mix. Removable membranes may be glass, plastic, rubber, etc. Kits may also be supplied with instructional materials. Instructions may be printed on paper or other substrates, and/or may be supplied as an electronic-readable medium. Detailed instructions may not be physically associated with the kit; instead, a user may be directed to an internet web site specified by the manufacturer or distributor of the kit, or supplied as electronic mail.

The present invention further provides a method of cleansing the colon prior to colonoscopy or in preparation for other medical, radiologic, and/or surgical procedures, comprising administering orally a preparation comprising, per liter of fluid, the following components:
a) 0.15 to 1.5 grams of potassium bicarbonate;
b) 1.0 to 3.5 grams of sodium bicarbonate;
c) 1.0 to 4.0 grams of citric acid;
d) 0.1 to 1.0 grams of sodium chloride;
e) 50.0 to 140.0 grams of a commercially available PEG; and
f) 1.0 to 50.0 grams of a minimally-fermentable sugar alcohol selected from a group that includes xylitol, erythritol, ribitol, arabitol, and mixtures thereof.

In an additional preferred embodiment, the patient may take a dose of a stimulant laxative 4 to 6 hours prior to ingesting the lavage solution. Stimulant laxatives cause rhythmic muscle contractions in the large intestines. This category of laxatives includes, without limitation: bisacodyl, senna, senekot, or cascara sagrada. Of course, larger or smaller doses may be used, as necessary, to produce a bowel movement within less than about 6 hours, while avoiding unnecessary discomfort.

In one preferred method according to the invention, a patient first takes 10 to 40 mg of bisacodyl tablets as a stimulant laxative at least 4-6 hours from beginning the liquid cleansing solution the evening prior to a scheduled examination. After about 6 hours, or preferably after having experienced a bowel movement in response to the bisacodyl, the patient reconstitutes one (1) liter of solution by pouring the sachet(s) of the unit dose of the dry composition mixture in a suitable container, pitcher, or bottle, and then adding one liter of water or other aqueous medium. After stirring for a few minutes and allowing the effervescence to occur, the patient consumes the reconstituted aqueous solution at a rate of about 250 ml (8 ounces) every 10 to 15 minutes until the entire one liter volume has been consumed, preferably within one hour. On the day of the planned procedure and at least four hours before the time scheduled for the examination, the patient repeats the same steps as above: preparing and mixing the sachet(s) of the second unit dose of the dry composition in one (1) liter of water or other aqueous medium and consuming the entire volume of the aqueous solution at a rate of about 250 ml (8 ounces) every 10 to 15 minutes until completed.

In another preferred method, and particularly useful for a procedure planned later in the day, a patient takes 10 to 40 mg of bisacodyl (Dulcolax®) only the evening before the examination. On the morning of the examination and a minimum of about six hours before the time of the scheduled procedure, the patient reconstitutes both unit doses of dry mixture of the composition in two (2) liters of water or other aqueous medium. As in the previous method, the solution is stirred and the effervescence allowed to occur, and the solution is then consumed at a rate of about 250 ml (8 ounces) every 10 to 15 minutes until the entire 2 liters have been consumed.

EXAMPLES

The following examples are included to demonstrate preferred embodiments of the invention. It should be appreciated by those of skill in the art that the formulations and techniques disclosed in the examples which follow represent those discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example #1

A preferred embodiment was formulated and mixed in 1 liter of distilled water. The preferred embodiment contained 0.688 grams of potassium bicarbonate, 2.1 grams of sodium bicarbonate, 2.0 grams of citric acid, 1.0 gram of sodium chloride, 120.0 grams of PEG, and 2.0 grams of xylitol. The weight ratio of PEG to xylitol in this preferred embodiment was 60:1, and the calculated osmolality 277 mOsm/kg. The concentration of electrolytes in the solution was determined with a Beckman D×C 600i Synchronous Access Clinical System automated analyzer. The resulting solution had a sodium concentration of 43 mmol/L, a chloride concentration of 17 mmol/L, a potassium concentration of 7 mmol/L, and a bicarbonate concentration of 16 mmol/L.

Example #2

In a pilot study, two healthy volunteers consumed 2 liters of the preferred isotonic solution as described in Example 1 in a split-dose fashion. An adequate purge was accomplished in both subjects with no significant cramping, nausea, or vomiting. Blood was obtained prior to and the morning after consuming the preparation. The results of this blood work are displayed in Tables I and II. Paired sample testing confirmed that there were no statistically significant differences in electrolytes, kidney function or serum calcium at the 0.05 alpha level.

TABLE I

Subject #1 (56 yo male) Isotonic Prep

|      | Prior Prep | After Prep |
|------|------------|------------|
| Gluc | 97         | 84         |
| Na   | 138        | 140        |
| K    | 4.6        | 4.1        |
| Cl   | 102        | 100        |
| C02  | 29         | 29         |
| BUN  | 13         | 12         |
| Cr   | 0.8        | 0.8        |
| Ca   | 9.3        | 9.2        |
| Alb  | 4.3        | 4.1        |

TABLE II

Subject #2 (52 yo female) Isotonic Prep

|      | Prior Prep | After Prep |
|------|------------|------------|
| Gluc | 91         | 96         |
| Na   | 140        | 138        |
| K    | 4.4        | 4.1        |
| Cl   | 104        | 103        |
| C02  | 29         | 29         |
| BUN  | 12         | 5          |
| Cr   | 0.8        | 0.8        |
| Ca   | 9.1        | 9.2        |
| Alb  | 3.7        | 4.0        |

Example #3

In a pilot study, a healthy volunteer consumed the preferred embodiment in a split dose fashion as described in the hypertonic formulation of the invention. This embodiment contained 0.688 grams of potassium bicarbonate, 2.1 grams of sodium bicarbonate, 2.0 grams of citric acid, 1.0 gram of sodium chloride, 68.0 grams of PEG, and 30.0 grams of xylitol reconstituted in 1 liter of water. The weight ratio of PEG to xylitol of this preferred embodiment was 2.3:1 and the calculated osmolality 355 mOsm/kg. An even more effective purge occurred with this formulation, and no significant cramping, nausea or vomiting occurred as a result of ingesting the solution. Blood work to assess the serum electrolytes, kidney function, and serum calcium were obtained prior to and after completing the solution. No significant differences were noted in these labs as shown in Table III.

TABLE III

Subject #1 (56 yo male) Hypertonic Prep

|      | Prior Prep | After Prep |
|------|------------|------------|
| Gluc | 92         | 85         |
| Na   | 139        | 143        |
| K    | 4.6        | 4.8        |
| Cl   | 13         | 12         |
| C02  | 29         | 32         |
| BUN  | 13         | 12         |
| Cr   | 0.8        | 0.9        |
| Ca   | 9.6        | 9.6        |
| Alb  | 2.2        | 2.6        |

Example #4

Ten healthy volunteers were given 10 cc samples both the electrolyte replenishing solution (comprising 0.688 grams of potassium bicarbonate, 2.1 grams of sodium bicarbonate, 2.0 grams of citric acid, 1.0 gram of sodium chloride dissolved in 1 liter of distilled water), as well as a preferred embodiment of the invention (comprising 0.688 grams of potassium bicarbonate, 2.1 grams of sodium bicarbonate, 2.0 grams of citric acid, 1.0 gram of sodium chloride, 120.0 grams of PEG, and 2.0 grams of xylitol dissolved in 1 liter of distilled water) and asked to match the perceived saltiness of each respective solution to one of four reference saline solutions, 0.1%, 0.2%, 0.3%, and 0.4% by weight sodium chloride in water. Sixty percent (60%) of those tasting the electrolyte replenishing solution selected the 0.2% saline solution as being the closest in taste in terms of perceived saltiness. On the preferred formulation trial, 50% chose the 0.3% saline solution and 40% the 0.2% solution in terms of perceived saltiness. None of the subjects selected the 0.4% saline solution as closest in taste to either solution in terms of perceived saltiness. The results of the experiment are summarized in Table IV.

TABLE IV

Perceived Saltiness of Solutions (10 volunteers)

| Comparative Solutions | # selecting 0.1% NaCl | # selecting 0.2% NaCl | # selecting 0.3% NaCl | # selecting 0.4% NaCl |
|---|---|---|---|---|
| Electrolyte replenishing solution | 2 | 6 | 2 | 0 |
| Preferred formulation | 1 | 4 | 5 | 0 |

Example 5

Seventy volunteers were asked to taste, in a blinded fashion, 2 ml samples of each of three solutions presented in random order that included the present invention, Golytely®, and MoviePrep®. The preferred embodiment of the invention utilized in this portion of the studies contained 0.688 grams of potassium bicarbonate, 2.1 grams of sodium bicarbonate, 2.0 grams of citric acid, 1.0 gram of sodium chloride, 120.0 grams of PEG, and 2.0 grams of xylitol reconstituted in 1 liter of water. Each blinded sample was ranked as #1) the most salty, #2) the least salty, #3) the most palatable (most likely to consume 64 ounces), and #4) the best tasting. Chi-square tests were to compare the results. The present invention was the preferred solution with a p value <0.001, and the results are summarized in Table V.

TABLE V

Blinded Taste Test (70 subjects)

|  | Solution A (Invention) | Solution B (Golytely) | Solution C (MoviePrep) | p value |
|---|---|---|---|---|
| Most Salty | 0 | 46 (66%) | 23 (34%) | <.001 |
| Least Salty | 65 (93%) | 2 (3%) | 3 (4%) | <.001 |

TABLE V-continued

Blinded Taste Test (70 subjects)

|  | Solution A (Invention) | Solution B (Golytely) | Solution C (MoviePrep) | p value |
|---|---|---|---|---|
| Most Palatable | 49 (70%) | 6 (9%) | 15 (21%) | <.001 |
| Best Tasting | 38 (54%) | 6 (10%) | 26 (37%) | <.001 |

Example #6

Forty-three healthy adults scheduled for routine outpatient colonoscopy, and who had a history of prior intolerance of other commercially-available colon cleansing solutions and/or sensitivity to laxatives or salty tastes elected to try this new composition. Patients with significant medical problems, heart disease, diabetes, or any potentially serious GI conditions were not offered the solution. A successful bowel preparation was achieved in all but one patient (a 97.7% success rate), and only one patient did not complete the solution due to transient nausea and vomiting (2.3% side effects). This compares favorably with the previously published results of other commercially-available colon cleansing solutions in the prior art, where an 80% success rate and an overall discomfort rate of 8% has been reported (DiPalma J A, *The American J Gastro*, 104:2275-2284, 2009). No clinically significant treatment-related changes were observed in vital signs (blood pressure or heart rate), hydration status, or blood chemistry values in subjects receiving either preparation. Of particular importance is the lack of any significant changes in the levels of serum chloride, sodium, or bicarbonate as a result of ingesting this lower chloride formulation. Other than the single patient noted above who experienced some transient vomiting, there were no other reports of abdominal cramping, nausea, bloating, or vomiting as a result of ingesting the formulation. The invention overall was found to be effective, well tolerated, and well received in this otherwise sensitive population.

Example #7

Breath hydrogen and methane levels were obtained from 142 patients immediately before undergoing routine outpatient colonoscopy. Patients had previously prepared for the examination by consuming one of the standard commercially-available colon cleansing solutions or the composition of the invention as described in Example #6 above. The results of this comparison are summarized in Table VI.

TABLE VI

Breath Hydrogen and Methane Following Standard Colon Cleansing Agents*

|  | Nulytley | Movieprep | Miralax/Gatorade | Invention (2 gm Xylitol) | Invention (30 gm Xylitol) |
|---|---|---|---|---|---|
| No. patients | 27 | 42 | 31 | 23 | 19 |
| Range breath $H_2$ | 0-12 | 0-93 | 2-44 | 2-79 | 2-43 |
| Average breath $H_2$ | 10.4 | 26.3 | 20.4 | 18.0 | 15.4 |
| Range breath $CH_4$ | 0-9 | 0-56 | 0-11 | 0-46 | 0-13 |
| Average breath $CH_4$ | 2.6 | 5.0 | 2.4 | 6.1 | 2.4 |
| Ave $H_2$ + Ave $CH_4$ | 13.0 | 31.3 | 22.9 | 24.1 | 17.8 |

*Breath samples were obtained immediately before colonoscopy on 142 consecutive patients and the levels of breath hydrogen and methane determined with a Quintron Breathalyzer and expressed as parts per million (ppm).

Although the preferred embodiments of this invention have been described hereinabove in some detail, it should be appreciated that a variety of embodiments will be readily available to persons utilizing the invention for a specific end use. The description of the compositions and method of this invention is not intended to be limiting on this invention, but is merely illustrative of the preferred embodiment of this invention. Other compositions and methods which incorporate modifications or changes to that which has been described herein are equally included within this application. Additional objects, features and advantages of the present invention will become apparent by referring to the above description of the invention.

I claim:

1. A dry composition comprising:
   a) between about 0.15-1.5 grams of potassium bicarbonate per liter of colon cleansing solution;
   b) between about 1.0-3.5 grams of sodium bicarbonate per liter of colon cleansing solution;
   c) between about 1.0-4.0 grams of citric acid per liter of colon cleansing solution;
   d) between about 0.1-1.0 grams of sodium chloride per liter of colon cleansing solution;

e) between about 50-140.0 grams of polyethylene glycol per liter of colon cleansing solution; and
f) between about 1.0-50.0 grams of a sugar alcohol selected from the group consisting of xylitol, erythritol, ribitol, arabitol and mixtures thereof per liter of colon cleansing solution;
wherein the dry composition upon reconstitution in an aqueous diluent produces an electrolyte replenishing colon cleansing solution.

2. A dry composition which upon reconstitution in an aqueous diluent produces an electrolyte replenishing colon cleansing solution comprising:
a) between about 0.15-1.5 grams of potassium bicarbonate per liter of aqueous diluent;
b) between about 1.0-3.5 grams of sodium bicarbonate per liter of aqueous diluent;
c) between about 1.0-4.0 grams of citric acid per liter of aqueous diluent;
d) between about 0.1-1.0 grams of sodium chloride per liter of aqueous diluent;
e) between about 50-140.0 grams of polyethylene glycol per liter of aqueous diluent; and
f) between about 1.0-50.0 grams per liter of aqueous diluent of a sugar alcohol selected from the group consisting of xylitol, erythritol, ribitol, arabitol and mixtures thereof.

3. A dry composition which upon reconstitution in an aqueous diluent produces an electrolyte replenishing colon cleansing solution comprising polyethylene glycol and
a) between about 10-60 mEq of Na+ ions per liter of aqueous diluent;
b) between about 1.5-15 mEq of K+ ions per liter of aqueous diluent;
c) between about 10-60 mEq of HCO3- ions per liter of aqueous diluent; and
d) between about 1.5 to 20 mEq of Cl— per liter of aqueous diluent.

4. The dry composition of claim 3, further comprising citric acid.

5. The dry composition of claim 3, further comprising a sugar alcohol.

6. The dry composition of claim 1, wherein the colon cleansing solution does not contain a purgative amount of sulfate or phosphate.

7. The dry composition of claim 1, wherein the dry composition upon reconstitution in an aqueous diluent produces a sodium and potassium electrolyte replenishing colon cleansing solution.

8. The dry composition of claim 1, wherein the polyethylene glycol and the sugar alcohol are each present in an amount sufficient to exhibit osmotic activity.

9. The dry composition of claim 1, wherein the polyethylene glycol and the sugar alcohol are each present in an amount sufficient to exhibit purgative activity.

10. The dry composition of claim 1, wherein the polyethylene glycol and the sugar alcohol are each present in an amount sufficient to increase stool volume.

11. The dry composition of claim 1, wherein the electrolyte replenishing colon cleansing solution contains between 1.5 and 20 mEq of chloride ions per liter of aqueous diluent.

12. The dry composition of claim 1, wherein the colon cleansing solution contains between 15 and 20 mEq of chloride ions per liter of aqueous diluent.

13. The dry composition of claim 1, wherein the polyethylene glycol has a molecular weight between about 2000 and 8000 Daltons.

14. The dry composition of claim 1, wherein the polyethylene glycol is PEG-3350.

15. The dry composition of claim 1, wherein the sugar alcohol is xylitol.

16. The dry composition of claim 1, wherein the dry composition comprises between about 4.0-50.0 grams of a sugar alcohol.

17. The dry composition of claim 1, wherein the combination of polyethylene glycol and the sugar alcohol comprises at least about 90% by weight of said composition.

18. The dry composition of claim 1, wherein the ratio of grams of polyethylene glycol to sugar alcohol is between about 2:1-60:1, 1.2:1-3.75:1 or 25:1-75:1.

19. The dry composition of claim 1, wherein the citric acid is anhydrous citric acid.

20. The dry composition of claim 1, wherein the sodium bicarbonate and the citric acid are present in amounts effective to produce tri-sodium citrate.

21. The dry composition of claim 1, wherein the aqueous diluent is water.

22. The dry composition of claim 1, further comprising a flavoring agent.

23. The dry composition of claim 22, wherein the flavoring agent is selected from the group consisting of kola nut extract, cherry flavor extract, caramel flavor extract, anise oil, cinnamon oil, vanilla, vanillin, cocoa, chocolate, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil, citrus oil, lemon oil, orange oil, lime oil, grapefruit oil, fruit essence, apple fruit essence, pear fruit essence, peach fruit essence, berry fruit essence, wildberry fruit essence, date fruit essence, blueberry fruit essence, kiwi fruit essence, strawberry fruit essence, raspberry fruit essence, cherry fruit essence, plum fruit essence, pineapple fruit essence, and apricot fruit essence.

24. The dry composition of claim 1, wherein 2 liters of the electrolyte replenishing solution are sufficient to cleanse the colon.

25. The dry composition of claim 1, wherein the citric acid is separated from the bicarbonate.

26. The dry composition of claim 1, wherein the citric acid is present in a sachet.

27. An electrolyte replenishing colon cleansing solution comprising:
a) between about 0.15-1.5 grams/liter of potassium bicarbonate;
b) between about 1.0-3.5 grams/liter of sodium bicarbonate;
c) between about 1.0-4.0 grams/liter of citric acid;
d) between about 0.1-1.0 grams/liter of sodium chloride;
e) between about 50-140.0 grams/liter of polyethylene glycol; and
f) between about 1.0-50.0 grams/liter of a sugar alcohol selected from the group consisting of xylitol, erythritol, ribitol, arabitol and mixtures thereof.

28. An electrolyte replenishing colon cleansing solution comprising polyethylene glycol and
a) between about 10-60 mEq of Na+ ions per liter;
b) between about 1.5-15 mEq of K+ ions per liter;
c) between about 10-60 mEq of HCO3- ions per liter; and
d) between about 1.5 to 20 mEq of Cl— per liter.

29. The colon cleansing solution of claim 28, further comprising citric acid.

30. The colon cleansing solution of claim 28, further comprising a sugar alcohol.

31. The colon cleansing solution of claim 27, wherein the colon cleansing solution has a perceived saltiness equivalent between about 0.1% to 0.3%.

32. The colon cleansing solution of claim 27, comprising between about 10-60 mEq of $Na^+$ ions; between about 1.5-15 mEq of $K^+$ ions; and between about 10-60 mEq of $HCO_3^-$ ions per liter of aqueous diluent.

33. The colon cleansing solution of claim 27, wherein said solution is substantially free of sulfate ions.

34. The colon cleansing solution of claim 27, wherein said solution is substantially free of phosphate ions.

35. The colon cleansing solution of claim 27, wherein said solution is substantially free of magnesium ions.

36. The colon cleansing solution of claim 27, further comprising a flavoring agent.

37. The colon cleansing solution of claim 36, wherein the flavoring agent is selected from the group consisting of kola nut extract, cherry flavor extract, caramel flavor extract, anise oil, cinnamon oil, vanilla, vanillin, cocoa, chocolate, menthol, grape, peppermint oil, oil of wintergreen, clove oil, bay oil, anise oil, eucalyptus, thyme oil, cedar leave oil, oil of nutmeg, oil of sage, oil of bitter almonds, cassia oil, citrus oil, lemon oil, orange oil, lime oil, grapefruit oil, fruit essence, apple fruit essence, pear fruit essence, peach fruit essence, berry fruit essence, wildberry fruit essence, date fruit essence, blueberry fruit essence, kiwi fruit essence, strawberry fruit essence, raspberry fruit essence, cherry fruit essence, plum fruit essence, pineapple fruit essence, and apricot fruit essence.

38. A method for cleansing a patient's colon in preparation for colonoscopy or a diagnostic, medical, surgical, or radiological procedure, comprising administering to the patient an effective amount of the colon cleansing solution of claim 27, thereby cleansing the patient's colon.

39. The method of claim 38, wherein the solution is administered as a split dose regimen.

40. The method of claim 39, wherein a first dose of solution is administered in the evening prior to the colonoscopy or procedure and wherein a second dose of solution is administered either in the evening before or the morning of the colonoscopy or procedure.

41. The method of claim 40, wherein the first dose comprises a one liter dose of solution.

42. The method of claim 40, wherein the second dose comprises a one liter dose of solution.

43. The method of claim 38, wherein the patient experiences breath methane levels of less than 6.1 ppm following administration of the solution.

44. The method of claim 38, wherein the patient experiences breath hydrogen levels of less than 18 ppm following administration of the solution.

45. A method for preparing a colon cleansing solution, comprising reconstituting the dry composition of claim 1 in an aqueous diluent.

46. The method of claim 45, wherein the aqueous diluent is water.

47. The method of claim 45, wherein citric acid is added separately to the solution to elicit effervescence.

48. A kit comprising the dry composition of claim 1.

49. The kit of claim 48, wherein the citric acid is separated from the bicarbonate.

50. The kit of claim 49, wherein the kit contains one or more sachets.

51. The kit of claim 50, wherein the citric acid is present in a first sachet.

52. The kit of claim 50, wherein the potassium bicarbonate, sodium bicarbonate, sodium chloride, polyethylene glycol and sugar alcohol are present in a second sachet.

53. The kit of claim 48, wherein the citric acid is present in tablet form.

54. The kit of claim 48, further comprising a container sufficient to hold a volume of at least about 1 liter of an aqueous solution.

* * * * *